US012390369B2

(12) United States Patent
Charles

(10) Patent No.: US 12,390,369 B2
(45) Date of Patent: Aug. 19, 2025

(54) OPHTHALMIC PROCEDURE CONTACT LENS WITH ENHANCED VITREOUS VISUALIZATION

(71) Applicant: Alcon Inc., Fribourg (CH)

(72) Inventor: Steven T. Charles, Memphis, TN (US)

(73) Assignee: Alcon Inc., Fribourg (CH)

( * ) Notice: Subject to any disclaimer, the term of this patent is extended or adjusted under 35 U.S.C. 154(b) by 418 days.

(21) Appl. No.: 17/938,579

(22) Filed: Oct. 6, 2022

(65) Prior Publication Data

US 2023/0157891 A1 May 25, 2023

Related U.S. Application Data

(60) Provisional application No. 63/281,298, filed on Nov. 19, 2021.

(51) Int. Cl.
*A61F 9/009* (2006.01)
*A61B 90/35* (2016.01)
A61B 90/30 (2016.01)
A61F 9/008 (2006.01)

(52) U.S. Cl.
CPC .............. *A61F 9/009* (2013.01); *A61B 90/35* (2016.02); *A61B 2090/306* (2016.02); *A61F 2009/00863* (2013.01); *A61F 2009/00874* (2013.01)

(58) Field of Classification Search
None
See application file for complete search history.

(56) References Cited

U.S. PATENT DOCUMENTS

| 3,780,979 A | 12/1973 | De Guillebon |
| 4,357,088 A | 11/1982 | Pomerantzeff |
| 5,312,396 A | 5/1994 | Feld |
| 5,909,270 A | 6/1999 | Moser |

(Continued)

FOREIGN PATENT DOCUMENTS

| AU | 2018274939 B2 | 6/2020 |
| CN | 210009227 U | 2/2020 |

(Continued)

OTHER PUBLICATIONS

Damodaran et al., "Digital micromirror device based ophthalmoscope with concentric circle scanning", 2017, pp. 2766-2780, vol. 8, No. 5, Biomedical Optics Express.

(Continued)

*Primary Examiner* — Shirley X Jian
(74) *Attorney, Agent, or Firm* — PATTERSON + SHERIDAN, LLP

(57) ABSTRACT

In certain embodiments, an ophthalmic procedure contact lens for ophthalmic treatment of an eye with a laser beam includes a frame, an objective lens, and an illumination ring. The frame has an eye end, an operator end, and a flange-like shape with an interior region. The eye end is configured to be disposed outwardly from the eye. The objective lens is disposed within the interior region of the frame. The objective lens transmits the laser beam through the eye end to treat the eye. The illumination ring is coupled to the frame and provides annular illumination through the eye end to illuminate the eye. The illumination ring includes a ring substrate and light emitters coupled to the ring substrate. The light emitters emit light.

13 Claims, 5 Drawing Sheets

(56) References Cited

U.S. PATENT DOCUMENTS

| | | | |
|---|---|---|---|
| 6,142,630 | A | 11/2000 | Koester |
| 6,322,556 | B1 | 11/2001 | Gwon |
| 6,789,900 | B2 | 9/2004 | Van De Velde |
| 7,374,287 | B2 | 5/2008 | Van De Velde |
| 7,510,282 | B2 | 3/2009 | Ueno |
| 7,520,613 | B2 | 4/2009 | Saito et al. |
| 7,703,922 | B2 | 4/2010 | Van De Velde |
| 8,480,659 | B2 | 7/2013 | Frey et al. |
| 8,652,602 | B1 | 2/2014 | Dolla |
| 8,783,868 | B2 | 7/2014 | Qiu |
| 8,876,808 | B2 | 11/2014 | Feklistov et al. |
| 8,994,753 | B2 | 3/2015 | Nakano |
| 9,033,500 | B2 | 5/2015 | Utsunomiya |
| 9,186,523 | B1* | 11/2015 | Zolli ............... A61N 1/36128 |
| 9,603,519 | B2 | 3/2017 | Bor et al. |
| 9,675,243 | B2 | 6/2017 | Sasak et al. |
| 9,789,002 | B2 | 10/2017 | Van De Velde |
| 10,130,511 | B2 | 11/2018 | Dantus |
| 10,478,342 | B2 | 11/2019 | Dick |
| 10,555,835 | B2 | 2/2020 | Schuele et al. |
| 10,799,107 | B2* | 10/2020 | Studer ............... A61F 9/009 |
| 2007/0258094 | A1 | 11/2007 | Izatt et al. |
| 2007/0291277 | A1 | 12/2007 | Everett |
| 2009/0073384 | A1 | 3/2009 | Warden |
| 2009/0137989 | A1 | 5/2009 | Kataoka |
| 2009/0196477 | A1 | 8/2009 | Cense et al. |
| 2010/0123873 | A1 | 5/2010 | Raymond |
| 2010/0152847 | A1 | 6/2010 | Padrick |
| 2011/0077557 | A1 | 3/2011 | Wing et al. |
| 2012/0033227 | A1* | 2/2012 | Bower ............... G01B 9/0203 356/479 |
| 2012/0281235 | A1 | 11/2012 | Murata |
| 2013/0102895 | A1* | 4/2013 | Gooding ............ A61F 9/00827 600/426 |
| 2013/0131652 | A1 | 5/2013 | Dick |
| 2013/0173029 | A1* | 7/2013 | Caldeira ............. G02C 13/001 700/79 |
| 2014/0058367 | A1 | 2/2014 | Dantus |
| 2014/0216468 | A1 | 8/2014 | Goldshleger |
| 2014/0232985 | A1* | 8/2014 | Yates ............... G06V 40/19 351/221 |
| 2014/0257257 | A1 | 9/2014 | Grant et al. |
| 2014/0268036 | A1 | 9/2014 | Ketterling et al. |
| 2014/0276674 | A1 | 9/2014 | Lee |
| 2015/0190278 | A1 | 7/2015 | Gooding |
| 2015/0342782 | A1 | 12/2015 | Mordaunt |
| 2016/0058617 | A1 | 3/2016 | Luttrull et al. |
| 2016/0074214 | A1 | 3/2016 | Palanker et al. |
| 2016/0074221 | A1 | 3/2016 | Tassignon et al. |
| 2016/0166431 | A1 | 6/2016 | Vogler et al. |
| 2016/0227999 | A1 | 8/2016 | An et al. |
| 2016/0235588 | A1 | 8/2016 | Hart et al. |
| 2016/0256324 | A1 | 9/2016 | Suzuki |
| 2016/0278629 | A1 | 9/2016 | Schuele |
| 2016/0302969 | A1 | 10/2016 | Yamamoto |
| 2017/0181625 | A1 | 6/2017 | Kawakami et al. |
| 2017/0181626 | A1* | 6/2017 | Shau ............... A61B 3/14 |
| 2017/0252213 | A1 | 9/2017 | Furuuchi et al. |
| 2017/0326003 | A1 | 11/2017 | Schuele et al. |
| 2018/0028354 | A1 | 2/2018 | Heeren |
| 2018/0028355 | A1 | 2/2018 | Raksi |
| 2018/0140257 | A1 | 5/2018 | Govindjee et al. |
| 2018/0206719 | A1 | 7/2018 | Adler et al. |
| 2018/0317767 | A1 | 11/2018 | Ryan |
| 2018/0353064 | A1 | 12/2018 | Soetikno et al. |
| 2018/0368915 | A1 | 12/2018 | Xia et al. |
| 2019/0159933 | A1 | 5/2019 | Romano et al. |
| 2019/0282403 | A1 | 9/2019 | Barrett et al. |
| 2019/0290124 | A1 | 9/2019 | Laforest et al. |
| 2019/0313903 | A1 | 10/2019 | Mckinnon |
| 2019/0365569 | A1 | 12/2019 | Skovgaard et al. |
| 2020/0038241 | A1 | 2/2020 | Wang et al. |
| 2020/0060873 | A1 | 2/2020 | Heeren |
| 2020/0085292 | A1 | 3/2020 | Fukuma et al. |
| 2020/0129336 | A1 | 4/2020 | Schuele et al. |
| 2020/0130103 | A1 | 4/2020 | Choi |
| 2020/0192080 | A1 | 6/2020 | Karam |
| 2020/0196853 | A1 | 6/2020 | Van Hemert et al. |
| 2020/0273218 | A1 | 8/2020 | Camino et al. |
| 2020/0397289 | A1 | 12/2020 | Ralston |
| 2020/0400422 | A1 | 12/2020 | Ralston |
| 2021/0100450 | A1 | 4/2021 | Amma |
| 2021/0186753 | A1 | 6/2021 | Al-Qaisi et al. |
| 2021/0275009 | A1 | 9/2021 | Yates |
| 2021/0378507 | A1 | 12/2021 | Wallace |
| 2021/0386586 | A1 | 12/2021 | Bor |
| 2022/0012459 | A1 | 1/2022 | Schwiegerling |
| 2022/0031511 | A1 | 2/2022 | Charles |
| 2023/0157889 | A1 | 5/2023 | Bor |

FOREIGN PATENT DOCUMENTS

| | | |
|---|---|---|
| CN | 108371542 B | 4/2020 |
| CN | 109196333 B | 12/2020 |
| CN | 111281651 B | 12/2020 |
| CN | 112862782 A | 5/2021 |
| CN | 112587302 B | 6/2021 |
| CN | 112587304 B | 6/2021 |
| DE | 19705044 A1 | 8/1998 |
| DE | 102019007147 A1 | 4/2021 |
| DE | 102019007148 A1 | 4/2021 |
| EP | 0770370 A2 | 2/1997 |
| EP | 1212022 B1 | 3/2005 |
| EP | 1563785 A1 | 8/2005 |
| EP | 1638452 B1 | 10/2006 |
| EP | 1838212 A1 | 10/2007 |
| EP | 2144552 A1 | 1/2010 |
| EP | 1928297 B1 | 11/2010 |
| EP | 2459138 A2 | 6/2012 |
| EP | 2525706 A2 | 11/2012 |
| EP | 2898820 A1 | 7/2015 |
| EP | 3061429 A1 | 8/2016 |
| EP | 2890340 B1 | 2/2017 |
| EP | 3459487 A1 | 3/2019 |
| EP | 3501463 A1 | 6/2019 |
| EP | 3636137 A1 | 4/2020 |
| EP | 3861924 A1 | 8/2021 |
| GB | 2469249 A | 10/2010 |
| JP | 5767014 B2 | 6/2015 |
| JP | 2017176558 A | 10/2017 |
| JP | 6410468 B2 | 10/2018 |
| JP | 2018196821 A | 12/2018 |
| JP | 2018196822 A | 12/2018 |
| JP | 2020022569 A | 2/2020 |
| JP | 6736304 B2 | 7/2020 |
| JP | 6839902 B2 | 2/2021 |
| RU | 2661016 C1 | 7/2018 |
| RU | 2692666 C1 | 6/2019 |
| RU | 2695629 C1 | 7/2019 |
| RU | 2710058 C2 | 12/2019 |
| RU | 2726468 C1 | 7/2020 |
| WO | 9958047 A1 | 11/1999 |
| WO | 0137769 A1 | 5/2001 |
| WO | 0195791 A1 | 12/2001 |
| WO | 2007059189 A2 | 5/2007 |
| WO | 2009033110 A2 | 3/2009 |
| WO | 2009036104 A2 | 3/2009 |
| WO | 2009039315 A2 | 3/2009 |
| WO | 2009059400 A1 | 5/2009 |
| WO | 2010117386 A1 | 10/2010 |
| WO | 2014053824 A1 | 4/2014 |
| WO | 2015131135 A1 | 9/2015 |
| WO | 2015171793 A1 | 11/2015 |
| WO | 2016033590 A1 | 3/2016 |
| WO | 2017062673 A1 | 4/2017 |
| WO | 2017196306 A1 | 11/2017 |
| WO | 2017205857 A1 | 11/2017 |
| WO | 2020074532 A1 | 4/2020 |
| WO | 2020180729 A1 | 9/2020 |
| WO | 2020215359 A1 | 10/2020 |
| WO | 2020216763 A1 | 10/2020 |
| WO | 2020257711 A1 | 12/2020 |
| WO | 2021023799 A1 | 2/2021 |
| WO | 2021049243 A1 | 3/2021 |

(56) References Cited

FOREIGN PATENT DOCUMENTS

| WO | 2021066047 A1 | 4/2021 |
|----|---------------|--------|
| WO | 2021092211 A1 | 5/2021 |
| WO | 2021183637 A1 | 9/2021 |
| WO | 2022149028 A1 | 7/2022 |
| WO | 2023089416 A1 | 5/2023 |
| WO | 2023089459 A1 | 5/2023 |
| WO | 2023097391 A1 | 6/2023 |

OTHER PUBLICATIONS

Fischer et al., "Scanning Laser Ophthalmoscopy (SLO)", In: Bille JF, editor. High Resolution Imaging in Microscopy and Ophthalmology: New Frontiers in Biomedical Optics [Internet], Aug. 14, 2019, accessed on Jan. 30, 2023 from https://www.ncbi.nlm.nih.gov/books/NBK554043, Springer.
Ginner et al., "Wide-Field OCT Angiography at 400 KHz Utilizing Spectral Splitting", Photonics, Oct. 23, 2014, pp. 369-379, vol. 1, No. 4.
Heidelberg Engineering GMBH, "Spectralis. Hardware Operating Instructions," Version 001, Aug. 2007.
Heidelberg Engineering, "Spectralis. Multimodal Imaging Platform Optimized for the Posterior Segment", accessed on Jan. 30, 2023 from https://business-lounge.heidelbergengineering.com/us/en/products/spectralis/spectralis/.
Hofer et al., "Dispersion encoded full range frequency domain optical coherence tomography", Jan. 5, 2009, pp. 7-24, vol. 17, No. 1, Optics Express, US.
Hofer et al., "Fast dispersion encoded full range optical coherence tomography for retinal imaging at 800 nm and 1060 nm", Mar. 1, 2010, pp. 4898-4919, vol. 18, No. 5, Optics Express.
Leitgeb et al., "Complex ambiguity-free Fourier domain optical coherence tomography through transverse scanning", 2007, pp. 3453-3455, vol. 32, Optics Letters.
Li et al., "DMD-based three-dimensional chromatic confocal microscopy", 2020, pp. 4349-4356, vol. 59, No. 14, Applied Optics.
Martial et al., "Programmable Illumination and High-Speed, Multi-Wavelength, Confocal Microscopy Using a Digital Micromirror", Aug. 2012, e43942, vol. 7, No. 8, Plos One.
Reznicek Lukas et al., "Wide-Field Megahertz OCT Imaging of Patients with Diabetic Retinopathy", Journal of Diabetes Research, 2015, 5 pages.
Ruggeri et al., "Imaging and full-length biometry of the eye during accommodation using spectral domain OCT with an optical switch", Jul. 1, 2012, pp. 1506-1520, vol. 3, No. 7, Biomedical Optics Express.
Sarunic et al., "Instantaneous complex conjugate resolved spectral domain and swept-source OCT using 3x3 fiber couplers", Feb. 2005, pp. 957-967, vol. 13, No. 3, Optics Express.
Shields et al., "Wide-angle Imaging of the Ocular Fundus", Review of the Ophthalmology, Feb. 15, 2003.
Singh, "Lasers Take Aim at Floaters", Ophthalmology Management, Jul. 1, 2019, pp. 38, 40-42, 59, vol. 23.
Singh, "Modern vitreolysis—YAG laser treatment now a real solution for the treatment of symptomatic floaters", Survey of Ophthalmology, Mar. 3, 2020, pp. 581-591, vol. 65, No. 5.
SunLED, NanoPoint-0201 Series LEDs, published Feb. 15, 2016, www.SunLEDusa.com.
Volk Optical, "Volk Idrees Mid-Vitreous Lens", Dec. 20, 2020, accessed on Dec. 20, 2020 from https://www.volk.com/...s?pr_prod_strat=collection_fallback&pr_rec_pid=4513049018402&pr_ref_pid=4513048952866&pr_seq=uniform.
Volk Optical, "Volk Singh Mid-Vitreous Lens", Dec. 20, 2020, accessed on Apr. 21, 2025 <https://www.volk.com/products/singh-mid-vitreous-vitreous-slit-lamp-lens>.
Wang et al., "In vivo full range complex Fourier domain optical coherence tomography", Jan. 30, 2007, 054103, vol. 90, Applied Physics Letters.
Wojtkowski et al., "Full range complex spectral optical coherence tomography technique in eye imaging", 2002, pp. 1415-1417, vol. 27, No. 16, Optics Letters.
Yasuno et al., "Simultaneous B—M-mode scanning method for real-time full-range Fourier domain optical coherence tomography", 2006, pp. 1861-1865, vol. 45, No. 8, Applied Optics.
Zhang et al., Removal of a mirror image and enhancement of the signal-to-noise ratio in Fourier-domain optical coherence tomography using an electro-optic phase modulator, Jan. 15, 2005, vol. 30, No. 2, Optics Letters.
Zhou et al., "Dual channel dual focus optical coherence tomography for imaging accommodation of the eye", May 25, 2009, pp. 8947-8955, vol. 17, No. 11, Optics Express.
Blake F. Webb, et al.; "Prevalence of vitreous floaters in a community sample of smartphone users"; Internat'l Journal of Ophthalmology; Jun. 18, 2013; pp. 402-405; 6(3); PMC/ US National Library of Medicine National Institutes of Health.
Chirag P. Shah, et al., YAG Laser Vitreolysis vs Sham YAG Vitreolysis for Symptomatic Vitreous Floaters a Randomized Clinical Trial, JAMA Ophthalmology, Sep. 2017, 918-923, 135-9.
Ellex Website, Treatment Guidelines—Laser Floater Removal; 2016, Ellex Medical Pty Ltd. E&OE. VB0002E, downloaded Apr. 20, 2017.
Felix Sauvage et al: "Photoablation of Human Vitreous Opacities by Light—Induced Vapor Nanobubbles", ACS Nano, vol. 13, No. 7, Jul. 9, 2019, pp. 8401-8416.
Kim Jihwan et al. "Nonmechanical Laser Beam Steering Based on Polymer Polarization Gratings: Design Optimization and Demonstration", Journal of Lightwave Technology, vol. 33, No. 10, pp. 2068-2077, May 15, 2015.
Michael J. Escuti, et al., "Geometric-Phase Holograms", Optics & Photonics News, pp. 22-29, Feb. 2016.
Milston Rebecca et al: "Vitreous floaters: Etiology, diagnostics, and management", Survey of Ophthalmology, vol. 61, No. 2, Mar. 1, 2016, pp. 211-227.
Nicusor Iftimia et al: "Hybrid retinal imaginer using line-scanning laser ophthalmoscopy and spectral domain optical coherence tomography", Optics Express, vol. 14, No. 26, Dec. 22, 2006.
Reece Bergstrom, et al., Vitreous Floaters, National Center for Biotechnology Information, May 21, 2020, 4 pages, Bookshelf ID NBK470420, StatPearls Publishing LLC, online.
Wikipedia Encyclopedia, Floater, Wikipedia Encyclopedia, Mar. 29, 2021, online: https://en.wikipedia.org/wiki/floater?wprov=sfti 1.
Zhang Yunbo et al: "Parallel large-range scanning confocal microscope based on a digital micromirror device", Optik vol. 124, No. 13 (2013), Aug. 4, 2012, pp. 1585-1588.
Adrian G.H. Podoleanu et al., Combined optical coherence tomograph and scanning laser ophthalmoscope mi nije dostupan besplatno., Electronics Letters, 34 (11), 1998.
Chi-Hung Lee, et al., Imaging vitreous floaters and cataracts with optical simulations, Optik, 194, 1-9, 2019.
Christy K. Sheehy et al., High-speed, image-based eye tracking with a scanning laser ophthalmoscope, Biomedical Optics Express, vol. 3, No. 10, 2012.
D. H. Kelly, "Retinal Inhomogeneity. II. Spatial Summation," J. Opt. Soc. Am., pp. 114-119, vol. 1, No. 1 (Jan. 1984).
D. H. Kelly, "Retinal Inhomogeneity. III. Circular-Retina Theory," D.H. Kelly, J. Opt. Soc. Am., pp. 810-819, vol. 2, No. 6 (Jun. 1985).
D.H. Kelly, "Visual Processing of Moving Stimuli," J. Opt. Soc. Am., pp. 216-225, vol. 2, No. 2 (Feb. 1985).
D.H. Kelly,, "Motion and Vision. II. Stabilized Spatio-Temporal Threshold Surface," J. Opt. Soc. Am., pp. 1340-1349, vol. 69, No. 10 (Oct. 1979).
D.H.Kelly, "Retinal Inhomogeneity. I. Spatiotemporal Contrast Sensitivity," J. Opt. Sec. Am., pp. 107-113, vol. 1, No. 1 (Jan. 1984).
Mojana F. et al., Observations by spectral-domain optical coherence tomography combined with simultaneous scanning laser ophthalmoscopy: imaging of the vitreous, American Journal of Ophthalmol. Apr. 2010; 149(4):641-650.
Nidek, Scanning Laser Ophthalmoscope Mirante SLO/OCT Mirante SLO, https://www.nidek-intl.com/product/ophthaloptom/diagnostic/dia_retina/mirante.htm.

(56) References Cited

OTHER PUBLICATIONS

Peter G. J. Barten, "Contrast Sensitivity of the Human Eye and its Effects on Image Quality," Model for the spatial contrast sensitivity of the eye, Chapter 3, pp. 27-40, (1999).
Pointer, J. S., & Hess, R. F. "The contrast sensitivity gradient across the human visual field: With emphasis on the low spatial frequency range,", R. F. Vision Research, 29(9), 1133-1151 (1989).
Sebag J et al., Vitreous and Vitreoretinal Interface, Ch. 21, 2015.
Sebag J., Vitreous and Vision Degrading Myodesopsia. Progress in Retinal and Eye Research Nov. 2020;79.
T Ivanova et al, Vitrectomy for primary symptomatic vitreous opacities: an evidence-based review, Eye (Lond) May 2016;30(5):645-55.
Teri T Kleinberg et al., Vitreous substitutes: a comprehensive review, Survey of Ophthalmology, 56 (4), 2011.

\* cited by examiner

OPHTHALMIC PROCEDURE CONTACT LENS WITH ENHANCED VITREOUS VISUALIZATION

CROSS-REFERENCE TO RELATED APPLICATIONS

This application claims priority to and benefit of U.S. Provisional Patent Application No. 63/281,298, filed Nov. 19, 2021, the entire contents of which are incorporated by reference herein in its entirety.

TECHNICAL FIELD

The present disclosure relates generally to ophthalmic systems, and more particularly to an ophthalmic procedure contact lens with enhanced vitreous visualization.

BACKGROUND

Vitreoretinal eye procedures are performed in the vitreoretinal region of the eye. Examples of such procedures include: breaking up vitreous clumped pre-existing collagen fibers ("floaters"); vitreous traction of a flap tear ("horseshoe tear") before in-office pneumatic retinopexy for limited retinal detachments; residual vitreoretinal traction after surgical vitrectomy; residual retinal tissue causing retinal detachment (elevation) due to incomplete surgical retinectomy; selected small diabetic traction retinal detachments; and selected vitreomacular traction syndrome cases.

A doctor must be able to see the vitreoretinal region in order to successfully perform a procedure. Moreover, appropriate illumination is key to effective vitreoretinal visualization. Unfortunately, in some situations, known systems fail to provide illumination that yields effective visualization.

BRIEF SUMMARY

In certain embodiments, an ophthalmic procedure contact lens for ophthalmic treatment of an eye with a laser beam includes a frame, an objective lens, and an illumination ring. The frame has an eye end, an operator end, and a flange-like shape with an interior region. The eye end is configured to be disposed outwardly from the eye. The objective lens is disposed within the interior region of the frame. The objective lens transmits the laser beam through the eye end to treat the eye. The illumination ring is coupled to the frame and provides annular illumination through the eye end to illuminate the eye. The illumination ring includes a ring substrate and light emitters coupled to the ring substrate. The light emitters emit light.

Embodiments may include none, one, some, or all of the following features:
  The light emitters comprise light sources, which may comprise light-emitting diode (LED) lights.
  The light emitters comprise optical fibers coupling a light source to the illumination ring, where an optical fiber delivers light from the light source to the illumination ring. The optical fiber may comprise a delivery fiber and an output fiber. The light source may provide a laser beam, such as a laser beam with a speckle pattern.
  The illumination ring is disposed between the objective lens and the eye.
  The objective lens is disposed within the illumination ring.
  The objective lens is a member of a set of interchangeable objective lenses, where at least two interchangeable objective lenses have different focus points.
  The ophthalmic procedure contact lens includes a controller that controls the illumination of the illumination ring. The controller may control a feature of light emitted by one or more of the light emitters and/or may control a pattern of illumination emitted by the light emitters.
  The objective lens is disposable.
  The illumination ring is disposable.

In certain embodiments, an ophthalmic procedure contact lens for ophthalmic treatment of an eye with a laser beam includes a frame, an objective lens, and an illumination ring. The frame has an eye end, an operator end, and a flange-like shape with an interior region. The eye end is configured to be disposed outwardly from the eye. The objective lens is disposed within the interior region of the frame. The objective lens transmits the laser beam through the eye end to treat the eye. The illumination ring is coupled to the frame and provides annular illumination through the eye end to illuminate the eye. The illumination ring includes a ring substrate and light emitters coupled to the ring substrate. The light emitters are light sources comprising light-emitting diode (LED) lights that emit light.
  Embodiments may include the following feature:
  The ophthalmic procedure contact lens includes a controller that controls the illumination of the illumination ring.

In certain embodiments, an ophthalmic procedure contact lens for ophthalmic treatment of an eye with a laser beam includes a frame, an objective lens, and an illumination ring. The frame has an eye end, an operator end, and a flange-like shape with an interior region. The eye end is configured to be disposed outwardly from the eye. The objective lens is disposed within the interior region of the frame. The objective lens transmits the laser beam through the eye end to treat the eye. The illumination ring is coupled to the frame and provides annular illumination through the eye end to illuminate the eye. The illumination ring includes a ring substrate and light emitters coupled to the ring substrate. The light emitters emit light and comprise optical fibers that couple a light source to the illumination ring. An optical fiber delivers light from the light source to the illumination ring, where the light source provides a laser beam.
  Embodiments may include the following feature:
  The light source provides a laser beam with a speckle pattern.

In certain embodiments, an ophthalmic procedure contact lens for ophthalmic treatment of an eye with a laser beam includes a frame, an objective lens, an illumination ring, and a controller. The frame has an eye end, an operator end, and a flange-like shape with an interior region. The eye end is configured to be disposed outwardly from the eye. The objective lens is disposed within the interior region of the frame, and transmits the laser beam through the eye end to treat the eye. The illumination ring is coupled to the frame and provides annular illumination through the eye end to illuminate the eye. The objective lens and the illumination ring are disposable. The illumination ring includes a ring substrate and light emitters coupled to the ring substrate. The light emitters emit light and include: light sources that include light-emitting diode (LED) lights; or optical fibers coupling a light source to the illumination ring, where an optical fiber comprises a delivery fiber and an output fiber that delivers light from the light source to the illumination ring and the light source provides a laser beam with a speckle pattern. The controller controls the illumination of the illumination ring by: controlling a feature of light emitted by one or more of the light emitters, and controlling a pattern of illumination emitted by the light emitters.

DESCRIPTION OF EXAMPLE EMBODIMENTS

Figure 1:
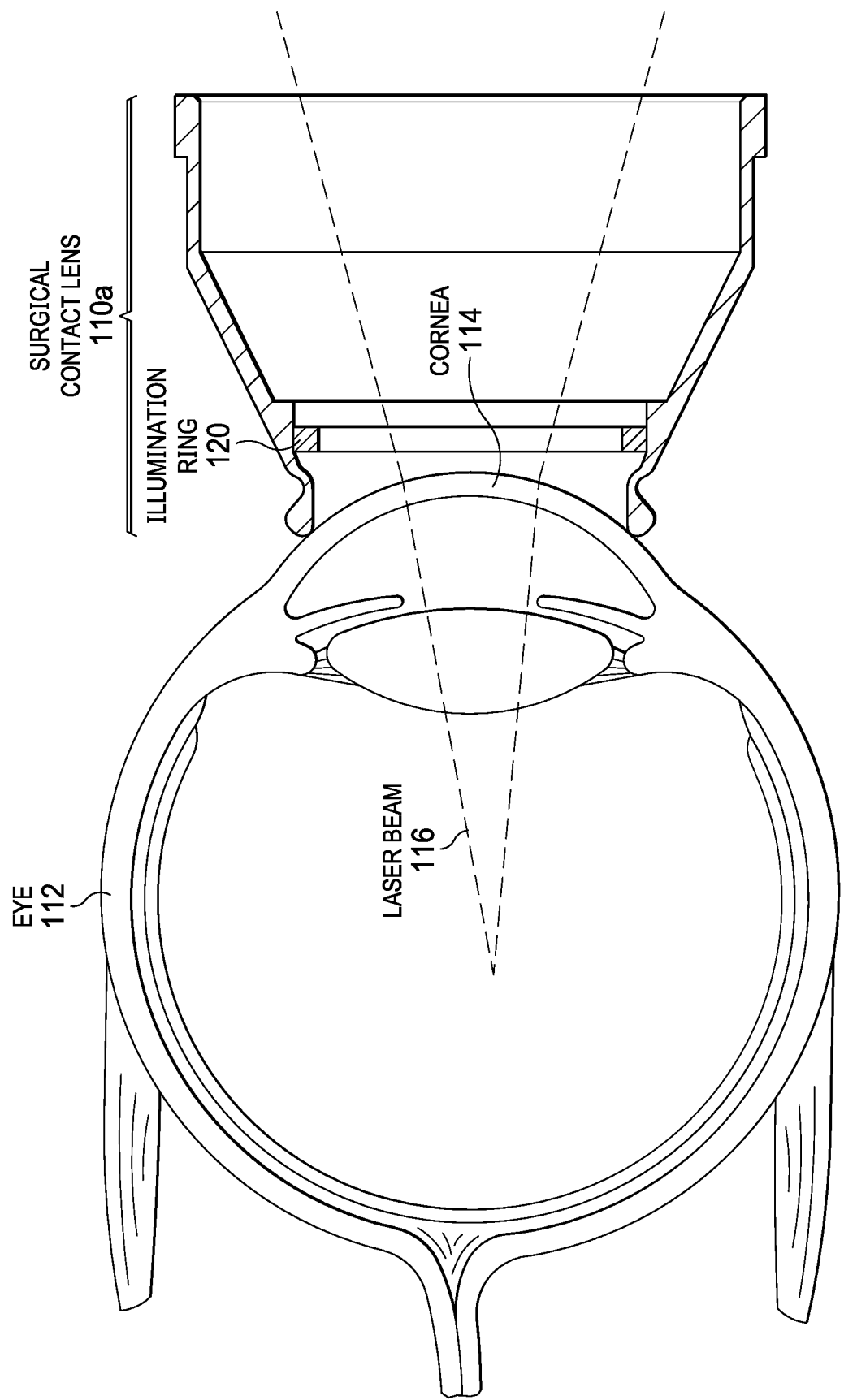
FIG. 1 illustrates an example of an ophthalmic procedure contact lens that enhances vitreous visualization, according to certain embodiments.

Referring now to the description and drawings, example embodiments of the disclosed apparatuses, systems, and methods are shown in detail. The description and drawings are not intended to be exhaustive or otherwise limit the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments.

Vitreoretinal visualization (i.e., visualization of the vitreous and/or retina) can be difficult because some targets, such as eye floaters, are almost transparent and absorb very little light. In addition, external illumination of the vitreoretinal area is limited by Purkinje images, which are reflections from the surfaces of the cornea and lens. Moreover, laser vitreoretinal procedures are typically real-time, see-aim-and-shoot procedures, so visualization should be in real-time, stereo, and in color. For example, when treating eye floaters, the doctor should have real-time visualization to see movement of the floaters in response to laser shots. In addition, the doctor should be able to see the lens and retina in stereo and in color, as they provide anatomic landmarks that prevent spatial disorientation.

These and other challenges render known vitreoretinal imaging techniques unsatisfactory in certain situations. Accordingly, an ophthalmic procedure contact lens that illuminates an eye with annular illumination is described herein. If the axis of the annular illumination is substantially coaxial with an axis of the eye (e.g., visual or optical axis), retinal reflections and Purkinje images may be reduced, thus enhancing vitreoretinal visualization.

FIG. 1 illustrates an example of an ophthalmic procedure contact lens 110 that enhances vitreous visualization, according to certain embodiments. As an overview, contact lens 110 is disposed outwardly from cornea 114 of eye 112. Contact lens 110 includes an illumination system implemented as an illumination ring 120. Illumination ring 120 provides annular illumination that enhances vitreous visualization. Laser beam 116 is transmitted through an optical element of contact lens 110 to treat eye 112.

Turning to the details, the illumination system provides light to illuminate at least a part or all of the vitreoretinal region, e.g., the vitreous and/or retina. The illumination light may be any suitable light, e.g., a laser beam such as a laser beam with an intrinsic spackle pattern. Optical elements 136 may modify the illumination light to yield any suitable illumination, e.g., one or more of the following types of illumination:

(1) Annular Illumination (AN): Annular illumination is light (e.g., white light-emitting diode (LED) light) provided as a tube or a hollow cone (such as a truncated cone), where light is absent from the interior. In an example of use, annular illumination strikes the eye as a ring located, e.g., just inside where sclera meets cornea. Annular illumination has an axis, e.g., the axis of the tube or cone of illumination. If the axis of the annular illumination is substantially coincident with an axis of the eye (e.g., visual or optical axis), retinal reflections and Purkinje images may be reduced.

(2) Multi-Beam Illumination (MB): Multi-beam illumination is light provided as a plurality of light beams, e.g., a plurality of laser beams. In certain embodiments, the multiple light beams may yield annular illumination. Multi-beam illumination enhances visualization of targets, e.g., vitreous floaters.

(3) Speckle Pattern (SP): The mutual interference of a set of coherent wavefronts of light (such as laser light) produce a speckle pattern. The speckle pattern enhances visualization of vitreous of targets, e.g., vitreous floaters. The speckle pattern may be used with any suitable optical configuration. For example, speckle pattern light may be provided as, e.g., a single beam, a slit beam, and/or multiple beams.

Figure 2:
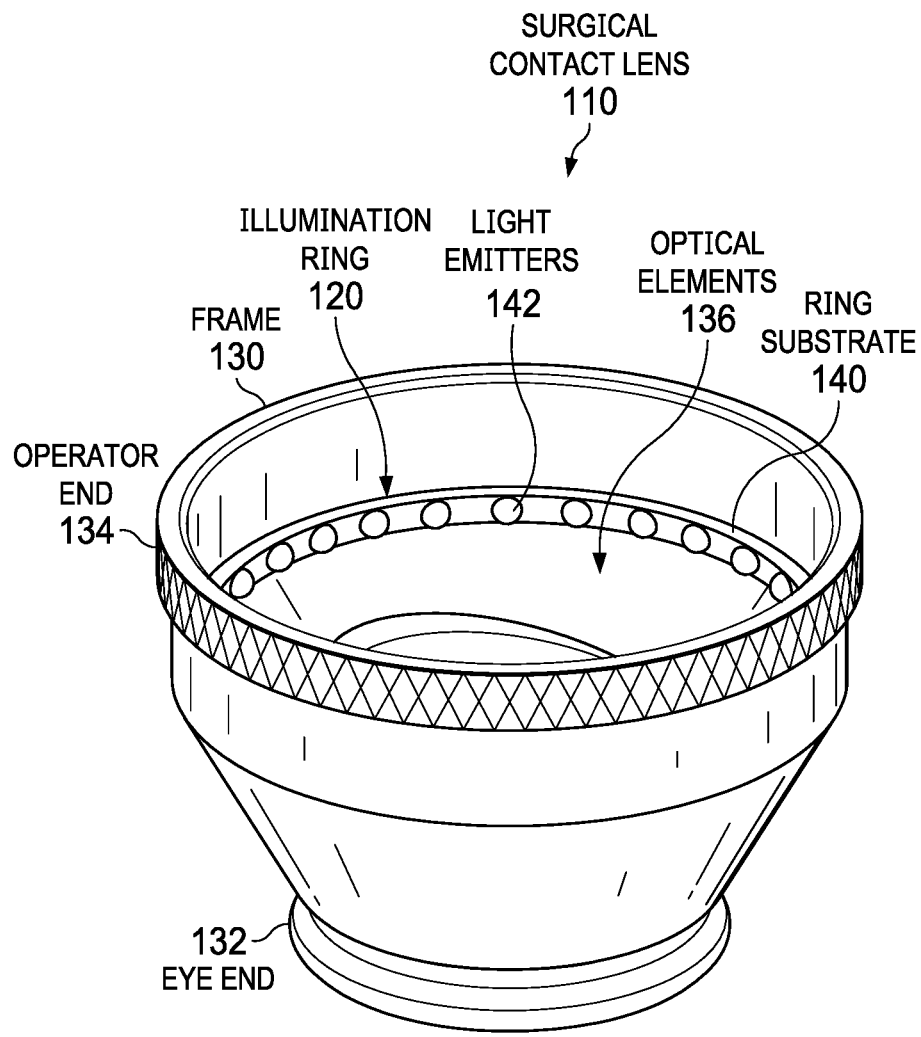
FIG. 2 illustrates an example of an ophthalmic procedure contact lens with an illumination ring, according to certain embodiments.

FIG. 2 illustrates an example of ophthalmic procedure contact lens 110 with illumination ring 120, according to certain embodiments. As an overview, contact lens 122 comprises a frame 130 with an eye end 132 and an operator end 134. Illumination ring 120 and optical elements 136 are coupled to and disposed within frame 132.

Examples of contact lens 122 include an ocular Singh mid-vitreous lens, a Peyman multi-segment lens, a Karickhoff off-axis lens, a Karickhoff four-mirror lens, and other frames with optical elements that allow an operator to view the interior of an eye. For example, a Singh mid-vitreous lens has a lens that provides views of the vitreous, e.g., from the lens posterior to the retina. As another example, a Peyman multi-segment lens may include separate lens inserts for viewing different regions of the eye, e.g., the anterior chamber to the posterior capsule, mid-vitreous, and deep vitreous. As another example, a Karickhoff off-axis lens has a lens that provides a view of an off-axis region of the eye. The operator rotates the lens to view other off-axis regions, without patient moving their eye.

As yet another example, a Karickhoff four-mirror lens has four mirrors and a central axis view. The mirrors are positioned at different angles to provide different fields of view of the eye interior. For example, 62° mirror provides a view of the peripheral fundus near the ora serrata; a 67° mirror provides a view from the equator to the mid ora serrata; a 76° mirror provides a view of the equator to the mid peripheral field; and an 80° mirror provides a view of the major vessel arcades. The fields of view may overlap so that areas from the central area to the periphery may be viewed by rotating the lens.

Turning to the details, a frame 130 has a flange-like shape (e.g., a skirt around an optical portion with a radius of curvature similar to that of, e.g., the eye, sclera, or cornea) with an interior region. Eye end 132 is to be disposed outwardly from eye 112. The scleral conjunctival contact surface may be treated with a sticky material to increase friction. A thixotropic fluid may be used. Operator end 134 is to be handled by an operator such as a doctor, and may have texture that allows the operator to easily handle end 134.

Optical elements 136 serve to magnify and/or focus the interior of eye 112. In general, an optical element transmits, refracts, reflects, or otherwise modulates light. In certain embodiments, optical elements 136 include one or more lens(es) and/or mirror(s) that magnify and/or focus the interior of eye 112. For example, optical elements 136 include an objective lens disposed within the interior region of frame 130. In general, an objective lens is an optical element that gathers light from an object and focuses the light rays to produce an image of the object. The objective lens of contact lens 110 transmits a laser beam through eye end 132 to treat an eye.

Illumination ring 120 provides annular illumination through eye end 132 to illuminate eye 112. In the example, illumination ring 120 includes a ring substrate 142 and light emitters 142 coupled to ring. Illumination ring 120 is described in more detail with reference to FIGS. 4A and 4B.

Figure 3A:
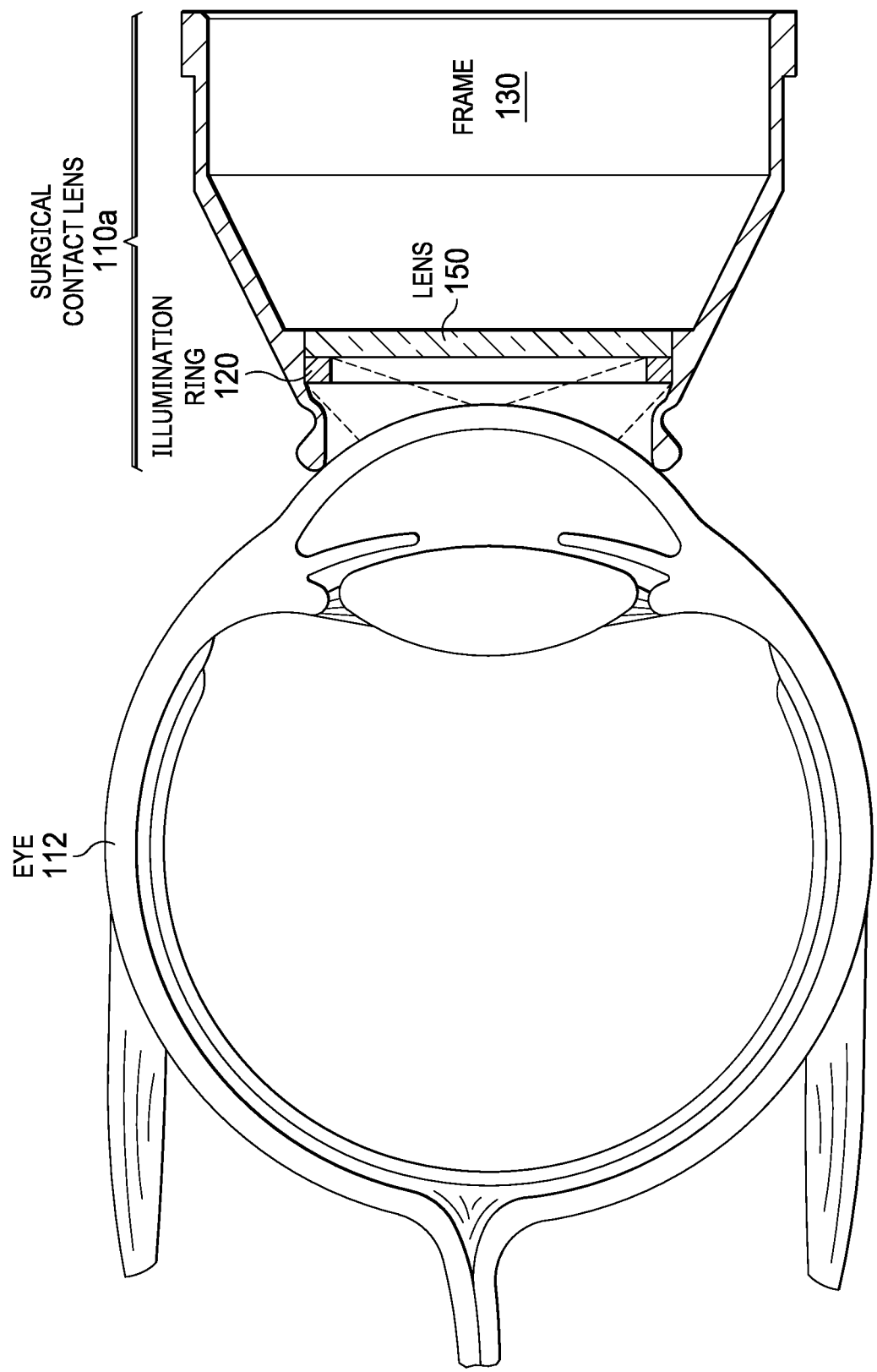
FIGS. 3A and 3B illustrate examples of ophthalmic procedure contact lenses with an illumination ring that illuminates an eye with annular illumination, according to certain embodiments.
Figure 3B:
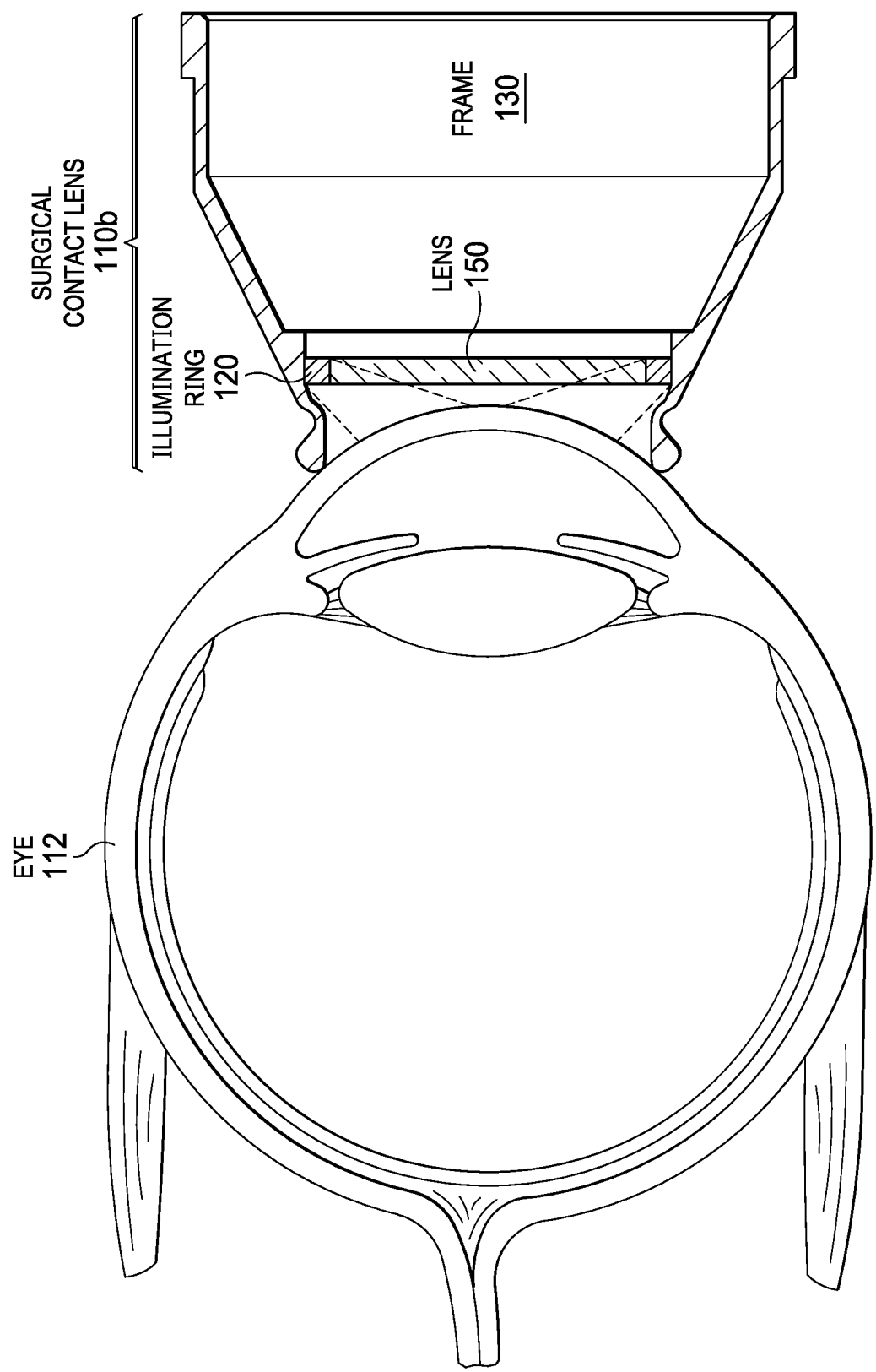

FIGS. 3A and 3B illustrate examples of ophthalmic procedure contact lenses 110 (110a and 110b) with illumination ring 120 that illuminates eye 112 with annular illumination, according to certain embodiments. In an example of use, annular illumination strikes the eye as a ring located, e.g., just inside where sclera meets cornea. If the axis of the annular illumination is substantially coaxial with an axis of the eye (e.g., visual or optical axis), retinal reflections and Purkinje images may be reduced. The annular illumination separates the illumination and visualization pathways similar to the Koehler principle in microscopy, which increases the contrast and visibility of floaters.

Turning to the specific examples, contact lens 110 includes an objective lens 150. In contact lens 110a of FIG. 3A, illumination ring 120 is disposed on the side of objective lens 150 closest to eye 112, i.e., between objective lens 150 and eye 112. In contact lens 110b of FIG. 3B, objective lens 150 is disposed within the interior region of illumination ring 120. These arrangements eliminate reflected light from the contact lens and cornea and reduce reflections from the lens or intraocular lens (IOL). Objective lens 150 gathers light from eye 112 and forms an image of eye 112 from the gathered light.

In certain embodiments, lens 150 may be a member of a set of interchangeable lenses, where different lenses 150 may have focus points at different depths of eye 112. For example, different lenses 150 may be used to focus on the anterior, mid, and posterior vitreous of eye 112. In certain embodiments, lens 150 may be disposable, or, in other embodiments, may be reusable after cleaning. Lens 150 may be formed in any suitable manner (e.g., by injection molding) with any suitable coating(s) (e.g., glare and/or anti-fogging coatings) and any suitable wafer-level optics.

Figure 4A:
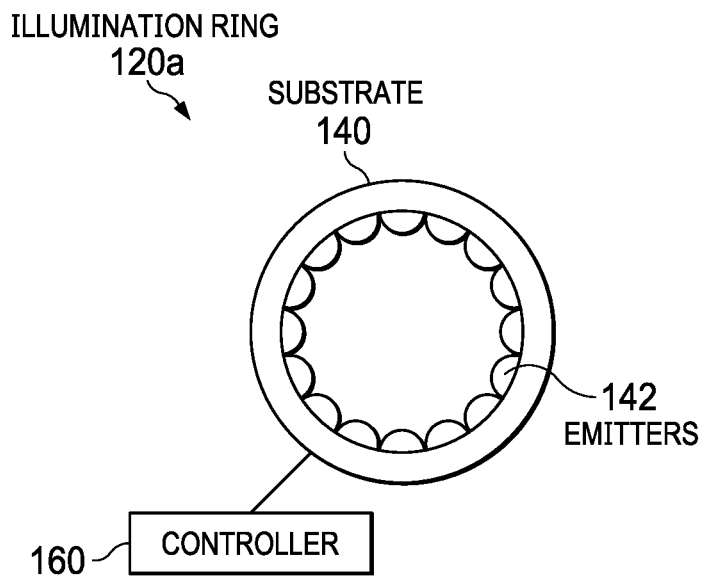
FIGS. 4A and 4B illustrate examples of illumination rings in communication with a controller, according to certain embodiments.
Figure 4B:
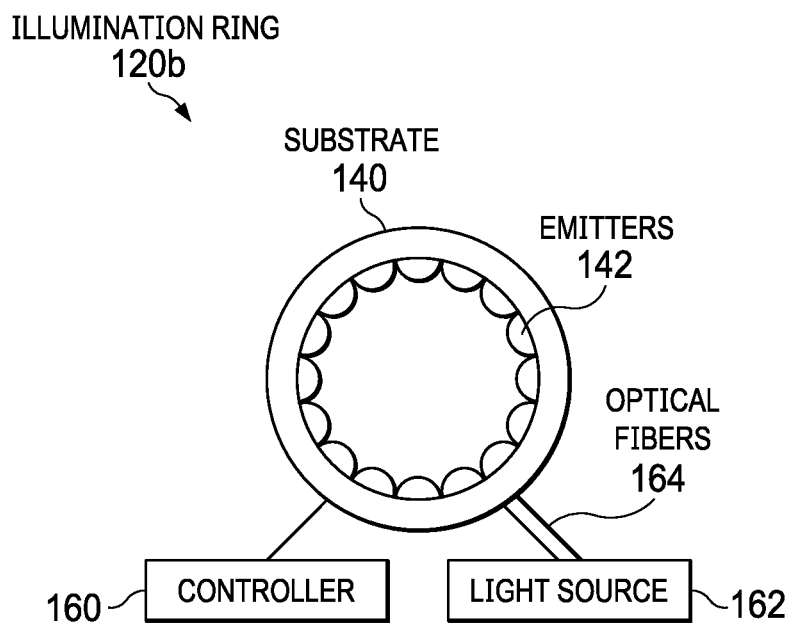

FIGS. 4A and 4B illustrate examples of illumination rings 120 (120a and 120b) in communication with a controller 160, according to certain embodiments. In the examples, illumination ring 120 (120a and 120b) includes a ring substrate 140 and light emitters 142, coupled as shown. Ring substrate 140 supports light emitters 142 and may have any suitable diameter to be disposed within frame, e.g., 1 to 3 centimeters. Light emitters 142 emit light to yield the annular illumination and may be arranged on ring substrate 140 in any suitable manner. For example, emitters 142 may be adjacent to each other or may be separated from each other. Generally, emitters 142 may be symmetrically and/or evenly distributed around ring substrate 140, but need not be in certain embodiments. Controller 160 may control the illumination of light emitters 142. Illumination ring 120b of FIG. 4B includes optical fibers 164 that couple a light source 162 to illumination ring 120b.

Turning to the specific embodiments, illumination ring 120a of FIG. 4A includes light emitters 142 that are light sources that generate light, e.g., light-emitting diode (LED) lights such as white or RGB micro-LED lights. Light emitter 142 may have any suitable dimensions, e.g., 0.1 to 3.0 millimeter (mm) in length, width, and height (e.g., 0.65 mm length×0.35 mm width×0.2 mm height). Light emitter 142 may have smaller dimensions achieved by future LED lights.

Illumination ring 120b of FIG. 4B includes light emitters 142 that are light outputs. In the example, light emitters 142 are the outputs of optical fibers that deliver light from light source 162 to illumination ring 120b. Light source 162 may be, e.g., a laser beam source that provides a laser beam, such as a laser beam with a speckle pattern. In certain embodiments, illumination ring 120 may be disposable and/or may be reusable after cleaning.

Optical fiber 164 may have any suitable features. As an overview, in certain embodiments, optical fiber 164 includes one or more optical fibers comprising a delivery fiber coupled to an output fiber, where the delivery fiber is coupled to light source 162 and the output fiber is coupled to substrate 140. In the embodiments, the delivery fiber may be a larger diameter fiber that delivers light from light source 162 to multiple output fibers. The output fibers may be smaller diameter fibers, such as nanofibers, with ends that emit the light.

Turning to the details of certain embodiments, the delivery fiber may have any features suitable for delivering light from light source 162 to the output fibers. In certain embodiments, the delivery fiber has a lower numerical aperture NA (e.g., 0.0 to 0.5) and a larger diameter (e.g., 50 to 100 micrometers) than that of the output fiber. An example of a delivery fiber is a multimode fiber. A multi-mode fiber has a large core diameter that enables multiple light modes to be propagated and that yields higher light-gathering capacity than a single mode fiber.

An output fiber may have any suitable features. In certain embodiments, the output fiber may be, e.g., a nanofiber (with a diameter in the nanometer range) or a micron fiber (with a diameter in the micrometer range). The distal end may have a numerical aperture NA of 0.5 to 1.0, a critical angle of 30 to 70 degrees, and a launch cone angle of 70 to 130 degrees (which is not output into the eye). For example, a 30-micron output fiber may have NA 0.66, critical angle 41.3°, and launch cone angle 82.6°. As another example, an output fiber may have NA 0.86, critical angle 59.32°, and launch cone angle 118.6°. The distal end may be tapered to provide the annular illumination.

Any suitable technique may be used to couple the delivery and output fibers to transport light from light source 162 to the output of emitters 142. Optical fiber 164 may include tapers, connectors (e.g., butt joint connections), and/or optical element(s) (e.g., lenses, transparent balls) to couple the fibers. When coupling the output and delivery fibers (plus taper or optical element), the radiometric A*omega product may be used to match the fibers. The A*omega product is the area A of the fiber cross-section times the solid angle NA of the light cone. The A*omega product of the delivery fiber should match the A*omega product of the output fiber.

Light emitters 142 may be used with any suitable optical elements to yield annular illumination (e.g., uniform annular illumination or a ring of beams). For example, the output fibers may be disposed along the periphery of substrate perpendicular or not perpendicular to the front surface of the contact. If the fibers are not perpendicular (e.g., are parallel) to the front surface, optical elements (e.g., molded prisms or light pipes) may be used to redirect the light towards the eye to yield annular illumination.

In certain embodiments, controller 160 controls the illumination of the illumination ring 120. Controller 160 may control one or more features of the light, e.g., intensity, wavelength (such as color), coherence, direction, and/or polarization. For example, controller 160 may instruct illumination ring 120 to use a blue light to decrease red reflex. Controller 160 may also control the pattern of light emitted by emitters 142. The pattern of light may include, e.g., which emitters 142 are emitting light, when and how long they emit light, and/or the features of the emitted light. For example, controller 160 may instruct illumination ring 120 to use multiple emitters 142 to yield multi-beam annular illumination. As another example, controller 160 may instruct illumination ring 120 to use a laser beam with a speckle pattern to enhance visualization.

A component (such as controller 160) of the systems and apparatuses disclosed herein may include an interface, logic, and/or memory, any of which may include computer hardware and/or software. An interface can receive input to the component and/or send output from the component, and is typically used to exchange information between, e.g., software, hardware, peripheral devices, users, and combinations of these. A user interface is a type of interface that a user can utilize to communicate with (e.g., send input to and/or receive output from) a computer. Examples of user interfaces include a display, Graphical User Interface (GUI), touchscreen, keyboard, mouse, gesture sensor, microphone, and speakers.

Logic can perform operations of the component. Logic may include one or more electronic devices that process data, e.g., execute instructions to generate output from input. Examples of such an electronic device include a computer, processor, microprocessor (e.g., a Central Processing Unit (CPU)), and computer chip. Logic may include computer software that encodes instructions capable of being executed by an electronic device to perform operations. Examples of computer software include a computer program, application, and operating system.

A memory can store information and may comprise tangible, computer-readable, and/or computer-executable storage medium. Examples of memory include computer memory (e.g., Random Access Memory (RAM) or Read Only Memory (ROM)), mass storage media (e.g., a hard disk), removable storage media (e.g., a Compact Disk (CD) or Digital Video or Versatile Disk (DVD)), database, network storage (e.g., a server), and/or other computer-readable media. Particular embodiments may be directed to memory encoded with computer software.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components, as apparent to those skilled in the art. As another example, modifications may be made to the methods disclosed herein. The methods may include more, fewer, or other steps, and the steps may be performed in any suitable order, as apparent to those skilled in the art.

To aid the Patent Office and readers in interpreting the claims, Applicants note that they do not intend any of the claims or claim elements to invoke 35 U.S.C. § 112(f), unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112(f).

What is claimed:

1. An ophthalmic procedure contact lens system for ophthalmic treatment of an eye with a laser beam, comprising:
    a frame with an eye end and an operator end, the frame having a flange-like shape with an interior region, the eye end configured to be disposed outwardly from the eye;
    an objective lens disposed within the interior region of the frame, the objective lens configured to transmit the laser beam through the eye end to treat the eye; and
    an illumination ring coupled to the frame and configured to provide annular illumination through the eye end to illuminate the eye, the illumination ring comprising:
    a ring substrate; and
    a plurality of light emitters coupled to the ring substrate, the plurality of light emitters configured to emit light, the plurality of light emitters comprising a plurality of optical fibers coupling a light source to the illumination ring, an optical fiber configured to deliver light from the light source to the illumination ring; and
    the light source configured to provide a laser beam with a speckle pattern.

2. The ophthalmic procedure contact lens system of claim 1, the optical fiber comprising a delivery fiber and an output fiber.

3. The ophthalmic procedure contact lens system of claim 1, the optical fiber comprising:
    a delivery fiber comprising a multimode fiber; and
    an output fiber comprising a nanofiber.

4. The ophthalmic procedure contact lens system of claim 1, the illumination ring disposed between the objective lens and the eye.

5. The ophthalmic procedure contact lens system of claim 1, the objective lens disposed within the illumination ring.

6. The ophthalmic procedure contact lens system of claim 1, the objective lens being a member of a plurality of interchangeable objective lenses, at least two interchangeable objective lenses having different focus points.

7. The ophthalmic procedure contact lens system of claim 1, further comprising a controller configured to control the illumination of the illumination ring.

8. The ophthalmic procedure contact lens system of claim 7, the controller configured to control a feature of light emitted by one or more of the plurality of light emitters.

9. The ophthalmic procedure contact lens system of claim 7, the controller configured to control a pattern of illumination emitted by the plurality of light emitters.

10. The ophthalmic procedure contact lens system of claim 1, the objective lens being disposable.

11. The ophthalmic procedure contact lens system of claim 1, the illumination ring being disposable.

12. An ophthalmic procedure contact lens for ophthalmic treatment of an eye with a laser beam, comprising:
- a frame with an eye end and an operator end, the frame having a flange-like shape with an interior region, the eye end configured to be disposed outwardly from the eye;
- an objective lens disposed within the interior region of the frame, the objective lens configured to transmit the laser beam through the eye end to treat the eye; and
- an illumination ring coupled to the frame and configured to provide annular illumination through the eye end to illuminate the eye, the illumination ring comprising:
  - a ring substrate; and
  - a plurality of light emitters coupled to the ring substrate, the plurality of light emitters configured to emit light, the plurality of light emitters comprising a plurality of optical fibers coupling a light source to the illumination ring, an optical fiber configured to deliver light from the light source to the illumination ring, the light source configured to provide a laser beam, the light source configured to provide a laser beam with a speckle pattern.

13. An ophthalmic procedure contact lens for ophthalmic treatment of an eye with a laser beam, comprising:
- a frame with an eye end and an operator end, the frame having a flange-like shape with an interior region, the eye end configured to be disposed outwardly from the eye;
- an objective lens disposed within the interior region of the frame, the objective lens configured to transmit the laser beam through the eye end to treat the eye;
- an illumination ring coupled to the frame and configured to provide annular illumination through the eye end to illuminate the eye, the illumination ring disposed between the objective lens and the eye or the objective lens disposed within the illumination ring, the objective lens being a member of a plurality of interchangeable objective lenses, at least two interchangeable objective lenses having different focus points, the objective lens being disposable, the illumination ring being disposable, the illumination ring comprising:
  - a ring substrate; and
  - a plurality of light emitters coupled to the ring substrate, the plurality of light emitters configured to emit light, the plurality of light emitters comprising:
    - a plurality of light sources comprising a plurality of light-emitting diode (LED) lights; or a plurality of optical fibers coupling a light source to the illumination ring, an optical fiber comprising a delivery fiber and an output fiber configured to deliver light from the light source to the illumination ring, the light source configured to provide a laser beam with a speckle pattern; and
- a controller configured to control the illumination of the illumination ring, the controller configured to control a feature of light emitted by one or more of the plurality of light emitters, the controller configured to control a pattern of illumination emitted by the plurality of light emitters.

* * * * *